(12) United States Patent
Krajewski et al.

(10) Patent No.: US 12,728,025 B2
(45) Date of Patent: Sep. 8, 2026

(54) WRIST BRACE

(71) Applicant: Essity Hygiene and Health Aktiebolag, Gothenburg (SE)

(72) Inventors: Stephan Krajewski, Hamburg (DE); Oliver Hass, Hamburg (DE); Emma Van Den Berg, Hengelo (NL); Daphne Gengler, Hengelo (NL)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 246 days.

(21) Appl. No.: 18/247,727

(22) PCT Filed: Nov. 9, 2021

(86) PCT No.: PCT/EP2021/081022
§ 371 (c)(1),
(2) Date: Apr. 3, 2023

(87) PCT Pub. No.: WO2022/096733
PCT Pub. Date: May 12, 2022

(65) Prior Publication Data

US 2023/0363933 A1 Nov. 16, 2023

(30) Foreign Application Priority Data

Nov. 9, 2020 (EP) .................................... 20206382

(51) Int. Cl.
*A61F 5/01* (2006.01)
*A61F 5/058* (2006.01)

(52) U.S. Cl.
CPC ........ *A61F 5/0118* (2013.01); *A61F 5/05866* (2013.01)

(58) Field of Classification Search
CPC ...... A61F 5/0118; A61F 5/05866; A61F 5/01; A61F 5/0102; A61F 5/0104; A61F 5/05;
(Continued)

(56) References Cited

U.S. PATENT DOCUMENTS 4,854,310 A * 8/1989 Lee ..................... A61F 5/05866 602/21
4,862,877 A 9/1989 Barber
(Continued)

FOREIGN PATENT DOCUMENTS

AU 2494399 A 8/1999
AU 199924943 A1 8/1999
(Continued)

OTHER PUBLICATIONS

Japanese Application No. 2023-526919; Office Action with English translation dated Jun. 18, 2024; 17 pages.
(Continued)

*Primary Examiner* — Keri J Nelson
(74) *Attorney, Agent, or Firm* — CANTOR COLBURN LLP

(57) ABSTRACT

The present invention relates to an orthosis adapted to be worn on a human forearm and hand for stabilizing the wrist joint, comprising a stiff body having an exostructure enclosing an elongated core, wherein the stiff body comprises (i) a metacarpal section, having a ring-shaped or ring-segment-shaped thumb holding section adapted to receive the thumb of the human hand, having a palmar section adapted to be brought into engagement with the palm of the human hand, and having a ulnar section adapted to wrap around the human hand from the volar to the dorsal side, (ii) an elongated middle section adapted to be brought into engagement with the human forearm on its medial or lateral side, and (iii) a forearm section adapted to wrap around the human forearm from its ventral to its dorsal side.

20 Claims, 8 Drawing Sheets

(58) Field of Classification Search
CPC ... A61F 5/058; A61F 5/05841; A61F 5/05858
See application file for complete search history.

(56) References Cited

U.S. PATENT DOCUMENTS

| | | | | |
|---|---|---|---|---|
| 5,713,837 | A | 2/1998 | Grim et al. | |
| 5,868,692 | A * | 2/1999 | Michniewicz | A61F 5/0118 602/20 |
| 5,921,945 | A | 7/1999 | Gray | |
| 6,024,712 | A | 2/2000 | Iglesias et al. | |
| 7,311,686 | B1 | 12/2007 | Iglesias et al. | |
| 9,463,108 | B2 * | 10/2016 | Anglada | A61F 5/0118 |
| 10,327,940 | B2 * | 6/2019 | Summit | A61F 5/0118 |
| 2005/0165338 | A1 | 7/2005 | Iglesias et al. | |
| 2007/0225629 | A1 * | 9/2007 | Israel | A61F 5/0118 602/5 |
| 2014/0330183 | A1 * | 11/2014 | Kazemtabrizi | A61F 5/0118 602/12 |
| 2015/0157483 | A1 * | 6/2015 | Grunden | A61F 5/013 602/22 |
| 2017/0231800 | A1 | 8/2017 | Ross et al. | |
| 2020/0078203 | A1 * | 3/2020 | Engelshoven | A61F 13/108 |

FOREIGN PATENT DOCUMENTS

| | | | |
|---|---|---|---|
| CA | 2241722 | A1 | 7/1997 |
| CA | 2398059 | A1 | 8/2001 |
| DE | 3006362 | A1 | 8/1981 |
| DE | 3519493 | A1 | 12/1986 |
| EP | 0876130 | A1 | 11/1998 |
| EP | 1052954 | A1 | 11/2000 |
| EP | 1265565 | A1 | 12/2002 |
| JP | 2000050258 | A | 2/2000 |
| JP | 2003522594 | A | 7/2003 |
| WO | 9724085 | A1 | 7/1997 |
| WO | 9938465 | A1 | 8/1999 |
| WO | 0160289 | A1 | 8/2001 |
| WO | 2013160478 | A1 | 10/2013 |
| WO | 2016020857 | A1 | 2/2016 |

OTHER PUBLICATIONS

PCT Notification of Transmittal of The International Preliminary Report on Patentability; International Application No. PCT/EP2021/081022; International Filing Date: Nov. 9, 2021; Date of Mailing: Jan. 24, 2023; pp. 1-16.

PCT Notification of Transmittal of The International Search Report and the Written Opinion of the International Searching Authority, or the Declaration; International Application No. PCT/EP2021/081022; International Filing Date: Nov. 9, 2021; Date of Mailing: Feb. 10, 2022; pp. 1-15.

PCT Written Opinion of the International Preliminary Examining Authority; International Application No. PCT/EP2021/081022; International Filing Date: Nov. 9, 2021; Date of Mailing: Oct. 13, 2022; pp. 1-7.

European Application No. 20206382.2-1122; European Office Action dated Nov. 7, 2023; 7 pages.

European Application No. 21806731.2-1122; European Office Action dated Jun. 16, 2023; 3 pages.

Vietnam Office Action w English Translation: Application No. 1-2023-02948; Date Mailed: May 15, 2025; pp. 1-4.

European Application No. 21806731.2-1122; European Office Action dated Jul. 28, 2025; 6 pages.

Japanese Application No. 2023-526919; Office Action with English translation dated Jan. 28, 2025; 17 pages.

Brazilian Application No. BR112023008506; Search Report dated Jun. 15, 2025; 4 pages.

Japanese Office Action, Application No. 2023526919, mailed Oct. 20, 2025, with English Translation, 10 pages.

Chinese Office Action, Application No. 202180075301.9, mailed Dec. 12, 2025, with English Translation, 12 pages.

* cited by examiner

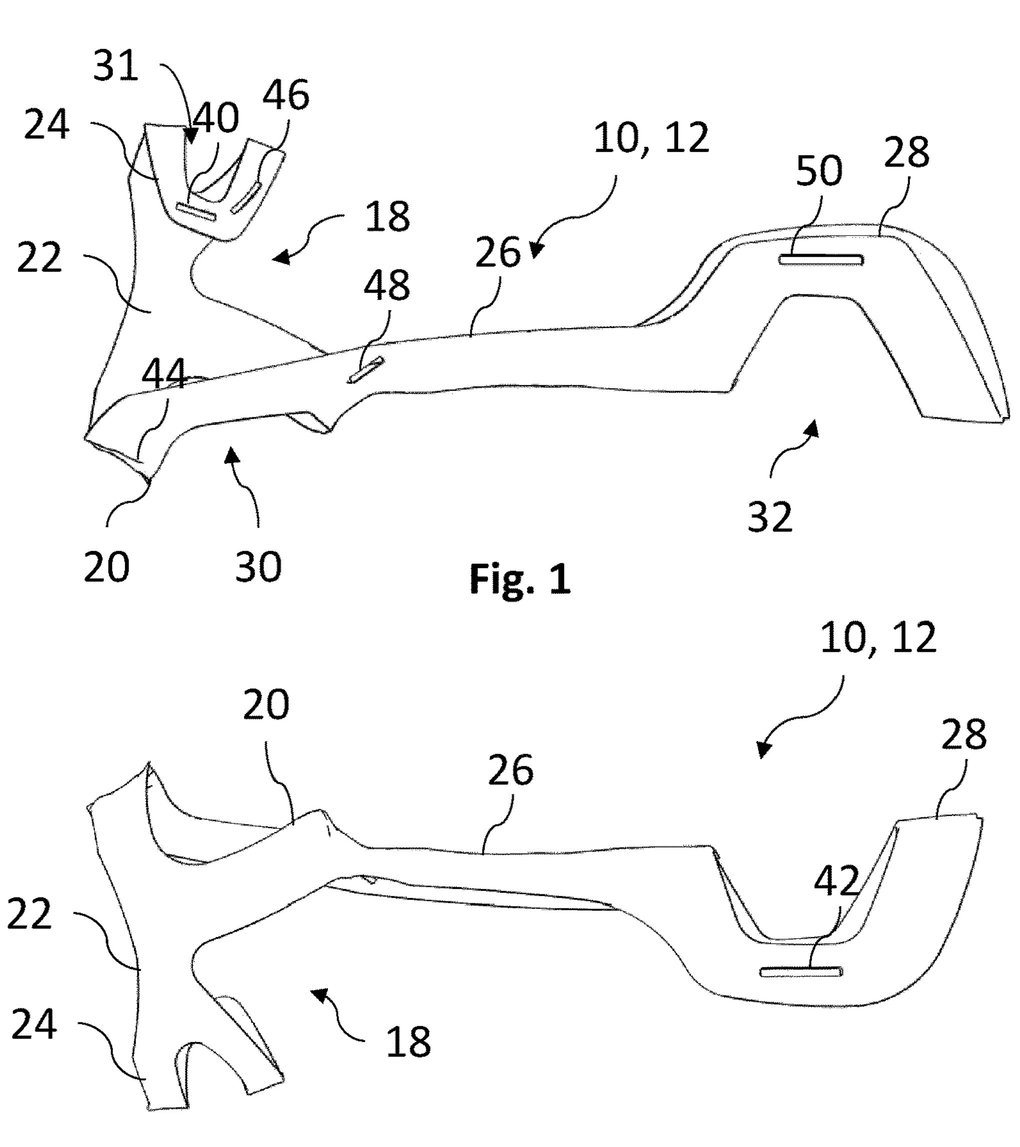
Fig. 1
10, 12
20
28
26
22
42
18
24
Fig. 2
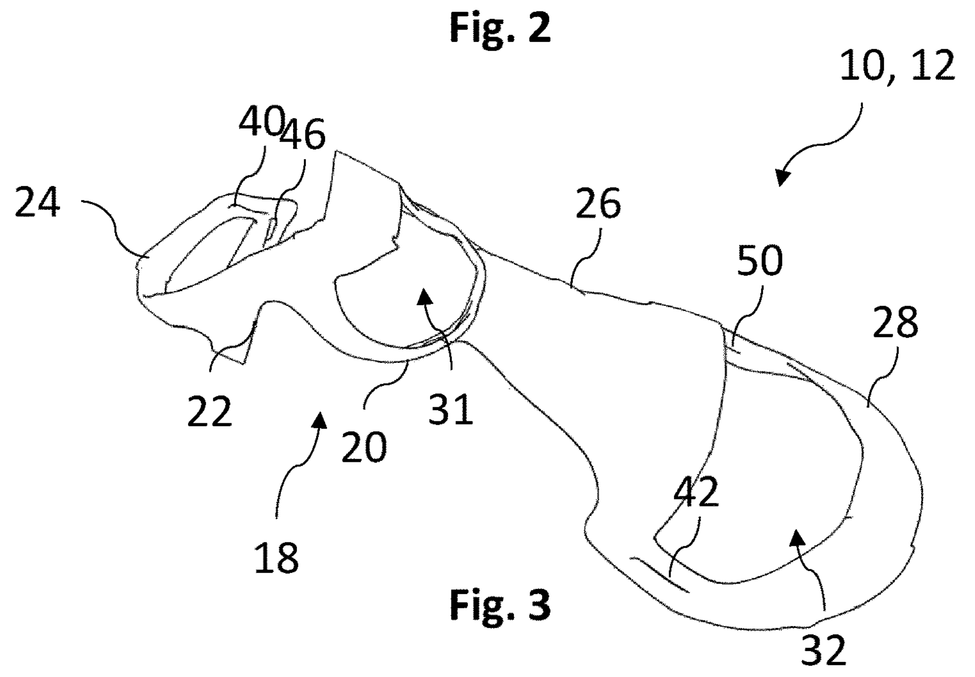
Fig. 3

31
40
46
24
10, 12
22
18
44
26
48
50
28
20
30
32

10, 12
30
20
28
26
42
22
40
46
18
24

10, 12
44
40
24
48
26
22
31
18
20
28
42
32

WRIST BRACE

CROSS-REFERENCE TO RELATED APPLICATIONS

This application is a National Stage application of PCT/EP2021/081022, filed Nov. 9, 2021, which claims the benefit of European Application No. 20206382.2, filed Nov. 9, 2020, both of which are incorporated by reference in their entirety herein.

TECHNICAL FIELD

The present disclosure relates to an orthosis adapted to be worn on a human forearm and hand for immobilizing the wrist joint as well as to a method for production of the orthosis.

BACKGROUND

Orthoses of this type are used to immobilize the wrist joint of a subject which suffers from a painful condition of the wrist or hand. The painful condition or injury can be caused by frequent, sustained repetitive motion of the hand or an acute accident. To allow the wrist to heal, it is desirable to reliably stabilize the joint in all directions of movement.

Known orthoses usually provide an extensive covering of the forearm and at least the palm of the hand for this purpose. The extensive covering has the disadvantage that it is very difficult to keep the body part clean. The patient can usually only wash the forearm when the orthosis is removed. However, during that time in which the orthosis is removed, the injured wrist is not stabilized. To promote the healing process, the orthosis should be worn as consistently as possible. Removal of the device should be avoided.

Further negative effects resulting from a long wearing time for common orthoses include itching and odour development. The aforementioned negative effects are enhanced by the textile portions of some orthoses which soil quite rapidly. These textile portions require regular, thorough washes and subsequent air drying during which the patient cannot wear the orthosis and is very limited in his or her daily activities.

Extensive coverage of the forearm and hand additionally blocks access to the affected wrist area that may be needed by a physician. In prior art orthoses, the physician can, therefore only examine the wrist, e.g. inspect surgical sites on the wrist, after the orthosis is removed. Each removal exposes the wrist to unwanted, detrimental movements.

There is, thus, a need in the art for improved wrist orthoses which provide the same level of stabilization, but allow for an improved hygiene, improved healing and better access to the wrist region.

SUMMARY

This problem is solved by the orthosis as described in the appended claims.

The present invention makes use of a washable, reversibly plastically deformable material that stabilizes the wrist in particular on the ulnar or radial side of the forearm and wrist. Thereby, the dorsal and ventral side of forearm and wrist can remain accessible for a physician.

In a first aspect, the invention, hence, relates to an orthosis adapted to be worn on a human forearm and hand for immobilizing the wrist joint, comprising a stiff body having an exostructure enclosing an elongated core, wherein the stiff body comprises (i) a metacarpal section,
  a. having a ring-shaped or ring-segment-shaped thumb holding section adapted to receive the thumb of the human hand,
  b. having a palmar section adapted to be brought into engagement with the palm of the human hand, and
  c. having an ulnar section adapted to wrap around the human hand from the hand's volar to the hand's dorsal side, (ii) an elongated middle section adapted to be brought into engagement with the human forearm, and, optionally, wrist, on their ulnar (medial) or radial (lateral) sides, and (iii) a forearm section adapted to wrap around the human forearm from its ventral to its dorsal side.

The orthosis of the invention is adapted to be worn on a human forearm and hand for stabilizing the wrist joint. This means that the orthosis has an elongated shape that runs along the forearm, wrist and hand of the wearer. The shape of the orthosis is anatomically adapted to fit to these body parts. The shape of the inner side of the orthosis can be shape-complementary to parts of the surface of the hand, wrist and forearm, in particular to parts of the metacarpal region of the hand, such as the palm of the hand, the ulnar (medial) or radial (lateral) side of the wrist and forearm and parts of the proximal end region of the forearm. The "inner side" of the orthosis is the side which faces the surface of the wearer's body when the orthosis is worn. The inner side can reside directly, i.e. can be adapted to reside directly, on the surface of hand, wrist and forearm, preferably at least 50%, at least 75% or at least 95% of the surface of the inner side. In other words, from 50% to 100% of the surface area of the inner side can be adapted to reside directly on the surface of the hand, wrist and forearm of the wearer, from 60% to 100%, from 70% to 100%, from 75% to 100%, from 80% to 100%, from 85% to 100%, from 90% to 100%, or from 95% to 100%.

The good fit of the orthosis is ensured by its ability to be plastically deformed and, thus, be adapted to the specific morphology of the individual wearer. The orthosis is, in other words, adaptable to the specific morphology of a wearer by plastic deformation, particularly by reversible plastic deformation. These properties and the high stability of the orthosis are ensured by the stiff body comprised in the orthoses which has an exostructure enclosing an elongated core. Suitable materials for exostructure and core are described elsewhere herein. In one embodiment, the stiff body consists of exostructure and core.

In particular, the elongated core is reversibly plastically deformable. A plastic deformation is caused by an applied force and—contrary to an elastic deformation—not undone simply by removing the force. The medical personnel donning the orthosis can, hence, bend the stiff body into the desired shape to adapt it to the individual patient's hand. The plastic deformation is, moreover, preferably reversible so that the orthosis can be adapted in case the initial fit has to be corrected. The term "plastic deformation" as used herein does, hence, not include a breaking of the stiff body. The bending of the core and stiff body which can be performed by the medical personnel is usually only a minor adaptation of the already existing basic shape of the stiff body which is established by the components of the stiff body described above (metacarpal section, middle section and forearm section), for example a slight bending of the stiff body in the palmar section to bring the surface of the inner side of the stiff body closer to the palm of the hand of the wearer.

The exostructure of the stiff body surrounds the plastically deformable core. The core is, in other words, embedded in the exostructure. Like the core, the exostructure can also be plastically deformable, but this is merely one alternative embodiment. In other embodiments, the exostructure is elastic, i.e. comprises or consists of an elastic material. The elastic material is adapted to ensure that the exostructure will deform as well when the core is being bent into the desired shape.

It is preferred that the exostructure covers 50% or more of the surface of the core, 60% or more, 70% or more, 80% or more, 90% or more, 95% or more, such as 100%. In other words, the exostructure covers from 50% to 100% of the surface of the core, 60% to 100%, 70% to 100%, 80% to 100%, 90% to 100%, or 95% to 100%. While the core will in most cases be entirely or substantially be covered by the exostructure, this may be influenced, e.g., by the method of production that is chosen for producing the stiff body. Uncovered sections of the core are, therefore, acceptable. Exemplary methods of production are described elsewhere herein.

The stiff body comprises (i) a metacarpal section, (ii) an elongated middle section and (iii) a forearm section. The sections are arranged in the orthosis in the aforementioned order and are, preferably, directly adjacent to each other. In other words, the metacarpal section is preferably directly adjacent to the middle section and the middle section is directly adjacent to the forearm section. In one embodiment, the stiff body consists of the metacarpal section, the elongated middle section and the forearm section. The stiff body is a one-piece construction. The exostructure is continuous in the stiff body, in particular the aforementioned metacarpal section, elongated middle section and forearm section. The exostructure is, thus, continuous from the ulnar section, the palmar section, the thumb holding section, the elongated middle section to the forearm section. This means that there are no gaps in the exostructure between the aforementioned sections. It will be understood that this does not exclude smaller production-based holes in the exostructure as long as the exostructure connects the aforementioned sections. The ulnar section's and thumb holding section's parts of the exostructure are not directly connected.

The term "stiff" means that the stiff body resists deformation by forces that are applied to the orthosis during normal use by the wearer. Thereby, the orthosis is able to keep the wrist joint in position. At the same time, the term "stiff" does not exclude that the stiff body can be bent, in particular plastically deformed as described above, when higher than normal forces are applied to the stiff body. It is, in fact, an advantageous property of the orthosis of the invention that it can be bent by the medical personnel donning the orthosis to adapt it to the hand and forearm of the wearer.

The orthosis comprises (i) a metacarpal section which is designed to wrap at least partially around the hand in its metacarpal region. The metacarpal section can be formed by at least one elongated element and at least partially encloses the metacarpal in a plane which, in the normal anatomical position of the hand and forearm, is essentially perpendicular to the longitudinal axis of the forearm. The metacarpal section is designed in such a way that it can be brought into engagement with a human hand by placing it at least partially around the back of the hand and in particular the palm of the hand below the metacarpal joints of the index finger, middle finger, ring finger and little finger and above the wrist so that it extends around the metacarpus in the circumferential direction and subsequently rests completely or partially against the palm and partially encompasses the metacarpal.

Preferably, the metacarpal section does not extend distally beyond the metacarpal region of the hand when the orthosis is worn. This improves mobility of the fingers of the wearer. The largest part of the metacarpal section will usually be designed to rest on the volar side of the hand of the wearer. The metacarpal section runs around one or both edges of the hand and lies completely or partially on one or both edges of the hand. It extends in the circumferential direction of the metacarpal over the entire palm of the hand or at least part of the palm, preferably the entire palm. It can lie completely or partially against the palm of the hand in order to provide a structure for immobilizing the flexion direction and the extension direction, i.e. preventing flexion and extension movements, and to prevent supination and pronation of the hand.

As a result of this configuration of the metacarpal section, the contact surfaces on the hand are advantageously arranged in the area of the metacarpal and at a distance from the wrist in the direction of the fingers when the brace is applied. The "contact surfaces" are in this context the surfaces of the stiff body, in particular the metacarpal region, e.g. the palmar region, which are in direct contact with the skin of the wearer, e.g. the skin of the hand of the wearer, i.e. which are adapted to be in direct contact with the skin of the wearer. Thus, the wrist is advantageously not covered on its volar and dorsal surface, so that these areas remain freely accessible to a sufficient extent and that no additional stress or pressure is exerted on a potential wound located in the region of the wrist.

Moreover, while the metacarpal section is wrapped around one or both sides of the hand, in particular the radial and ulnar sides, it will usually not extend over the entire width of the hand on its dorsal side (back of the hand). The metacarpal section can, for example, extend (i.e. be adapted to extend) over 100% of the circumference of the volar side of the metacarpal region of the hand, i.e. the palm, in radial to ulnar direction, and extend (i.e. be adapted to extend) over 0% to 50%, preferably 0% to 25%, of the circumference of the dorsal side of the metacarpal region of the hand, in radial to ulnar direction. There is, thus, a section of the dorsal side which is not covered by the metacarpal section or other parts of the stiff body. The coverage on the volar side of the hand provides a sufficient stability of the orthosis while the gap(s) on the dorsal side ensure good accessibility and easy cleaning of the hand. The gap(s) on the dorsal side can be closed by removable, flexible closure devices as described elsewhere herein.

The metacarpal section has (a) a ring-shaped or ring-segment-shaped thumb holding section adapted to receive the thumb of the human hand. The thumb holding section comprises a ring- or ring-segment-shaped opening adapted for receiving the thumb. Overall, the thumb holding section is designed in such a manner that, when the metacarpal section is brought into engagement with the hand, said thumb holding section can be placed against the thumb of the hand such that the thumb extends through the ring-shaped or ring-segment-shaped thumb holding section, i.e. through the ring opening defined by the thumb holding section, and that the thumb holding section then extends over at least part of the circumference of the thumb and entirely or at least partially surrounds the latter.

The thumb-holding section can, furthermore, wrap around the radial side of the hand. Thereby, the stability of the wrist brace is stably held on the hand even when the closure devices are not closed.

As the purpose of the orthosis is a stabilization of the wrist and not a stabilization of the thumb in particular, it will usually not extend along the thumb itself. The thumb can retain its movability at least in the interphalangeal joint. The orthosis is not adapted to cover this joint.

The metacarpal section has additionally (b) a palmar section adapted to be brought into engagement with the palm of the human hand. In a preferred embodiment, the palmar section extends over the palm substantially perpendicularly to the joint longitudinal axis of the forearm and hand. By means of this configuration of the palmar section, the latter, when placed on, is advantageously arranged in the region of the metacarpus and is at a distance from the wrist in the direction of the fingers. Therefore, the wrist is advantageously not covered and remains freely accessible for a physician if needed. The palmar section can, for example, be arranged in the palm of the hand below the metacarpophalangeal joints of an index finger, middle finger, ring finger and small finger.

On the opposite side of the palmar section from the thumb holding section, the metacarpal section comprises an ulnar section. The ulnar section is adapted to wrap around the human hand from the volar to the dorsal side, specifically on the ulnar side of the hand, i.e. the side of the fifth metacarpal bone. For this purpose, the ulnar section is curved and can have a cross-section of a semi-circle or semi-ellipse. The ulnar section can form one end of the metacarpal section of the orthosis and leave large parts of the back of the hand free, so that these parts of the back of the hand are not covered by a part of the stiff body. As will be described elsewhere herein, the ulnar section can be connected to the thumb holding section by means of closure devices which stretch over the back of the hand.

In its longitudinal direction, the metacarpal section has a first end which is formed by the thumb holding section which comprises one of the two longitudinal ends of the elongated element, and a second end which is formed by the ulnar section. The thumb holding section is preferably directly adjacent to the palmar section and/or the palmar section is directly adjacent to the ulnar section. The metacarpal section of the stiff body can consist of thumb holding section, palmar section and the ulnar section.

In addition to the metacarpal section, the stiff body also comprises (ii) an elongated middle section adapted to be brought into engagement with the human forearm and wrist on their ulnar or radial sides, or with the human forearm on its ulnar or radial side. Usually, the middle section will extend, i.e. will be adapted to extend, from the forearm into the wrist region. It may, in some cases, however, also be possible that the wrist is covered by the thumb section of the orthosis. In these cases, the elongated middle region is adapted to be brought into engagement with the human forearm. In most other cases the middle section will be adapted to be brought into engagement with the human forearm as well as the wrist.

It has been found in the context of the invention that this stabilization on one side of the wrist and forearm with the stiff body provides sufficient immobilization to promote healing of the wrist. It is not necessary to provide a stabilizing section on both, the ulnar and the radial side. The elongated middle section is, therefore, preferably arranged on one side of the forearm and wrist, i.e. adapted to be arranged on one side of the forearm and wrist, while the opposite side of wrist and forearm is freely accessible, i.e. not covered by any parts of the stiff body. In certain embodiments, the middle section is adapted to be arranged on the radial side of the forearm and wrist. The middle section can, thus, be directly adjacent to the thumb holding section of the metacarpal section. In these embodiments, the middle section will not be adjacent to the ulnar section of the metacarpal section. The ulnar section is preferably not directly connected to a section that extends to the forearm when the orthosis is worn. That way, the ulnar side and parts of the dorsal and ventral sides are freely accessible ensuring good ventilation of the skin and accessibility for medical personnel.

The middle section can be adapted to cover the wrist and/or forearm of a human on 50% or less, 45% or less, 40% or less, 35% or less, 30% or less, 25% or less, 20% or less, or 15% or less of their respective circumferences (in the section of the wrist and forearm, respectively, in which the middle section is located; preferably over the entire length of the middle section). This means, in other words, that only 50% or less, 45% or less, 40% or less, 35% or less, 30% or less, 25% or less, 20% or less, or 15% or less, of the surface of the wrist and/or forearm are covered by the middle section in the section of the limb on which the middle section is located. For example, the middle section can be adapted to cover the wrist and/or forearm of a human on from 5% to 50%, from 10% to 50%, from 5% to 45%, from 10% to 45%, from 5% to 40%, from 10% to 40%, from 5% to 35%, from 10% to 35%, from 5% to 30%, from 10% to 30%, from 5% to 25%, from 10% to 25%, from 5% to 20%, from 10% to 20%, from 5% to 15%, or from 10% to 15%, of their respective circumferences. Thereby, access to volar and dorsal surfaces of the wrist and forearm are ensured, in particular to the middle of the volar and dorsal sides of the wrist and forearm. The "middle" in this context is the area which extends along the longitudinal axis of the volar side or the longitudinal axis of the dorsal side. In one particular embodiment, the middle section is adapted to cover the wrist and/or forearm of a human on 50% or less of their respective circumferences. In another embodiment, the middle section is adapted to cover the wrist and/or forearm of a human on 25% or less of their respective circumferences. The middle section can, in other words, be adapted to cover the wrist and/or forearm of a human on 2% to 50%, 3% to 40%, 4% to 30% or 5% to 25% of their respective circumferences.

The shape of the middle section is adapted to the shape of the forearm of a human wearer. The middle section of the orthosis can have the form of the curved walls of a partial cylinder, e.g. a half-cylinder. The inner side of said cylinder forms the inner side of the middle section that is adapted to reside on the wearer's skin. A cross section of the middle section, thus, has the shape of a partial circle or partial oval. The partial circle or partial oval has a central angle of 5° or more, 10° or more, or 15° or more. At the same time, the central angle of the partial circle or partial oval is preferably 180° or less, 135° or less, 100° or less, or 90° or less. In certain embodiments, the central angle of the partial circle or partial oval is from 5° to 180°, such as from 10° to 100°.

To most efficiently stabilize the wrist, the middle section can extend along a considerable portion of the forearm. For example, the middle section can be long enough to ensure that the proximal end of the orthosis is located as close as possible to the elbow without interfering with the movement of the elbow joint. The length of middle and forearm sections together may be adapted to extend along 50% or more, 60% or more, 70% or more, 75% or more, 80% or more, 85% or more, or 90% or more of a forearm of a human wearer, wherein 60% or more is preferred, and 70% or more is particularly preferred. In other words, the length of middle and forearm sections together may be adapted to extend along from 50% to about 100%, from 60% to about 100%, from 70% to about 100%, from 75% to about 100%, from 80% to about 100%, from 85% to about 100%, or from 90% to about 100% of a forearm of a human wearer.

The middle section of the orthosis can be longer than the metacarpal section and/or the forearm section when measured parallel to the longitudinal axis of the orthosis. For example, the middle section can have a length that is 100% or more of the length of the metacarpal section, such as 125% or more, 150% or more, 175% or more, or 200% or more. In other words, the middle section can have a length that is from 100% to 300% or the length of the metacarpal section, such as from 125% to 300%, from 175% to 300%, from 200% to 300%, from 125% to 250%, from 150% to 250%, from 175% to 250%, from 200% to 250%. Similarly, the middle section can have a length that is 125% or more of the length of the forearm section, such as 150% or more, 175% or more, or 200% or more. In other words, the middle section can have a length that is from 125% to 300% of the length of the forearm section, such as from 150% to 300%, from 175% to 300%, from 200% to 300%, from 125% to 250%, from 150% to 250%, from 175% to 250%, from 200% to 250%. The lengths of the sections mentioned herein are measured parallel to the longitudinal axis of the orthosis.

The middle section can, for example, have a length of 7.5 cm or more, or 10 cm or more. In other words, the middle section can have a length of from 7.5 cm to 20 cm, from 10 cm to 18 cm. It will be understood that the absolute length will depend on the actual size of the orthosis which is individually chosen to fit a certain patient.

The stiff body, in particular its metacarpal section and/or middle sections, are adapted to establish a hand position suitable for contracture prophylaxis. Suitable angles in the wrist can e.g. be 20° to 30° dorsal extension. Accordingly, the stiff body, e.g. its metacarpal and/or its middle section, is adapted to establish an angle of 20° to 30° dorsal extension in the wrist of a wearer. This angle is particularly useful for stabilization and recovery of the wrist. As indicated above, the appropriate angle can be ensured by manual plastic deformation of the orthosis. It can also be preestablished in the orthosis.

Finally, the stiff body comprises a forearm section adapted to at least partially wrap around the human forearm from its ventral to its dorsal side. It wraps around the proximal forearm in a direction which is essentially perpendicular to the longitudinal axis of the stiff body, namely in a circumferential direction. The forearm section also forms the proximal end of the orthosis. By wrapping around and lying completely or partially against the forearm of the wearer, the forearm section provides at least one bearing for the stabilization of the wrist flexion, wrist extension, supination and pronation. Accordingly, the orthosis is suitable for reducing or preventing flexion, extension, supination and/or pronation movements of the wrist, wherein prevention of these movements is preferred. The length of the middle section and the forearm section as a bearing effectively ensure a stabilization against these movements. For this purpose, the forearm section is adapted to be close to the elbow when worn correctly, without preventing movement in the elbow joint. Particularly the supination and pronation movements of the wrist are effectively prevented by this combination of elongated middle section and forearm section.

In a direction that is perpendicular to the longitudinal axis of the stiff body, the forearm section is broader than the elongated middle section. The forearm section can, e.g., be adapted to cover the forearm of a human on 15% to 90%, preferably 25% to 90% of its circumference (in the section of the proximal forearm in which the forearm section is located; preferably over the entire length of the forearm section). In other words, the forearm section can be adapted to cover the forearm of a human on 15% or more, 25% or more, 35% or more, 45% or more, 50% or more of its circumference. This means that 15% to 90%, preferably 25% to 90%, of the surface of the forearm is covered by the forearm section in the section of the limb (arm) on which the forearm section is located.

To achieve this purpose, the shape of the forearm section is adapted to the shape of the forearm of a human wearer. The forearm section of the orthosis has the form of the curved walls of a partial cylinder, e.g. a half-cylinder. The inner side of said cylinder forms the inner side of the forearm section that is adapted to reside on the wearer's skin. A cross section of the forearm section, thus, has the shape of a partial circle or oval. The partial circle or oval has a central angle of 75° or more, 80° or more, 85° or more, 90° or more, 95° or more, 100° or more, 110° or more, 120° or more, 130° or more, 140° or more, 150° or more, 160° or more, 170° or more, or 180° or more, wherein 135° or more is preferred. At the same time, the central angle of the partial circle or partial oval is preferably 300° or less, 280° or less, 260° or less, 240° or less, 220° or less, 200° or less. In certain embodiments, the central angle of the partial circle or partial oval is from 100° to 260°, such as from 135° to 225°.

To improve the ability to clean the skin of hand, wrist and forearm and, thereby, the wearing comfort, the metacarpal section and/or the forearm section can comprise an opening. This is an opening in an otherwise larger area of material that is in addition to the opening generated by the ring-shaped or ring-segment shaped thumb-holding section. This/these additional opening(s) is/are preferably closed on all four sides and can, thus, be regarded as a window to the skin. The opening can have a rectangular shape with rounded edges, circle shape, oval shape, ellipsoid shape or irregular shape. An opening in the metacarpal section is envisaged to be located in the ulnar section. Together with the ulnar section, the opening can wrap around the ulnar edge of the hand. The opening will, thus, be on the ulnar side of the orthosis. Also, in the forearm section, the opening can be in the part of the forearm section that wraps around the forearm of the wearer. This opening will usually be on the radial side of the orthosis.

The orthosis of the invention can advantageously be adapted to the specific hand shape of the wearer, thus, increasing the efficiency of the orthosis, the wearing comfort and reducing the need for a high number of differently sized versions of the orthosis. Adaptation of the orthosis is effected through plastic deformation of the stiff body and corresponding adjustment of the closure devices described elsewhere herein. The stiff body, in particular its core, can, hence, be reversibly plastically deformable as indicated above. The plastic deformation is reversible because the term plastic deformation as used herein does not refer to an irreversible breaking of the product. Instead, the reversibility of the plastic deformation ensures that even after the first adaptation has been carried out by the medical personal, further adaptations, e.g. smaller corrections, can still be performed. The stiff body can also be bent back to its originally manufactured conformation.

The stiff body, in particular its core, can be plastically deformable at room temperature, i.e. 20° C. to 25° C. Thereby the need for further equipment and the number of donning steps is minimized. Alternatively, the stiff body can be plastically deformable at higher temperatures, such as 28° C. or more, 30° C. or more, 35° C. or more, 40° C. or more. Preferably, the temperature at which the stiff body is reversibly plastically deformable by medical personnel is low enough to be comfortable for a human patient, e.g. 55° C. or less, 50° C. or less, 45° C. or less. Cores which are reversibly plastically deformable at room temperature are, e.g., metal or metal alloy cores, such as an aluminium or aluminium alloy core.

Plastic deformability can, e.g., be achieved using one of the core materials that are described elsewhere herein. Alternatively or additionally, the structure of the stiff body, the exostructure and/or the core can be designed to allow for or support a plastic deformation. The stiff body, exostructure and/or core may, for example, have a deformable grid structure.

Adaptation of the stiff body to the hand of a wearer can be, e.g., achieved using a metal or thermoplastic material. Accordingly, the stiff body, core and/or exostructure, in particular the core, can comprise or consist of a metal and/or thermoplastic material. In the case of a thermoplastic material, the adaptation of the orthosis to a particular wearer will then be effected by applying heat to the thermoplastic material, adapting the stiff body to the wearer's hand, wrist and forearm and subsequent cooling of the material. As mentioned above, it is preferred that the required temperature is low enough to be comfortable for the wearer. However, it is also possible to adapt the orthosis stepwise removed from the surface of the body. In these cases, the required temperature for deformation can be higher.

In particular embodiments, the core may consist of or comprise one or more metals or metal alloys. Metals and metal alloys are particularly well suited to be used in a plastically deformable stiff body. The metal or metal alloys can be selected from the group consisting of aluminium, iron and alloys thereof, such as steel. In a particularly preferred embodiment, the core is an aluminium core, i.e. a core made from an aluminium alloy.

In further embodiments, the core may consist of one or more thermoplastic materials, in particular one or more low temperature thermoplastic materials. Low temperature thermoplastic materials are characterized by a deformation temperature lower than 100° C. (212° Fahrenheit), e.g. between 40° C. and 100° C. Suitable materials are known in the art and commercially available. They can be plastically deformed after or during heating in a water bath or the like, e.g. around temperatures of 70° C.

The core may be non-elastic at lower temperatures, specifically at temperatures from 20-30° C., such as room temperatures, or below. At these temperatures, the core is, moreover, resistant to tension and to bending.

The core can, for example, have a cylindrical, ellipsoid, oval, rectangular or irregular cross section. Preferably, the core has a cross-section having a longer width than height, e.g. an oval, ellipsoid or rectangular cross-section. Compared with cores with cross-sections that have equal width and height, the bending and stabilization properties are improved. The core can be arranged in the orthosis such that one of its cross-sectional sides having the longer width is oriented towards the inner side of the orthosis.

The core can extend from the metacarpal section, through the middle section and into the forearm section. The core does not have to be present in all areas of the exostructure, but it is preferred that it is comprised in metacarpal section, middle section and the forearm section. For example, certain areas of the metacarpal region do not need to comprise the core, such as the ulnar section and parts of the thumb holding section. It is, however, advantageous if at least parts of the thumb holding section and at least parts of the palmar section comprise core as well as exostructure. The core can be a single-piece design or a multi-piece design, wherein forming the core as one piece is preferred.

Depending on the material to be used in the core, the core can be manufactured e.g. by a method selected from the group of (i) dye cutting of metal blanc and subsequent bending of the core and (ii) dye cutting of the thermoplastic core and subsequent thermoforming of the core.

Similar to the core, the exostructure can comprise different materials. The materials of the exostructure can be more elastic as they are not the main stabilizers. They can be more flexible at room temperature. The materials of the exostructure will be selected for their ability to provide sufficient wearing comfort and at the same time facilitate an easy cleaning of the stiff body at room to body temperature (~20° C. to ~40° C.). At these temperatures, the material of the exostructure can be elastic. The exostructure will, therefore, have a closed surface structure that does not soak up water, i.e. a fluid-tight surface. The material of the exostructure will, moreover, have a good bio (skin) compatibility, media resistance, sweat resistance, alcohol resistance, disinfectant resistance and will be waterproof.

The exostructure can comprise or consist of thermoplastic polyurethane (TPU), thermoplastic elastomer (TPE), thermoplastic rubber (TPR), silicone and mixtures thereof. In a preferred embodiment, the exostructure comprises or consist of TPU. In one embodiment of the invention, the orthosis comprises a stiff body having an aluminium core and a TPU exostructure.

The stiff body can be manufactured by various methods known in the art. For example, the stiff body can be manufactured by a method selected from the group consisting of 2-component injection moulding, such as 2-component plastic injection moulding; multi-component plastic injection moulding; metal core overmoulding or plastic overmoulding in general and metal mesh overmoulding, wherein the method of metal core overmoulding, such as metal core blank overmoulding, is particularly preferred.

For fastening the orthosis on the human hand, the orthosis may comprise in addition to the stiff body one or more closure devices. The orthosis can, e.g. comprise 1, 2, 3, 4, 5, 6, or 7 closure devices, preferably two, more preferably three. For example, one or two of the closure devices may be attached to the metacarpal section, preferably two. One or two of the closure devices may be attached to the forearm section, preferably one. It will be understood that the stiff body can comprise corresponding attachment points, such as openings in which the closure devices can be fastened.

The closure devices can have, for example, one or more flexible or elastic bands which, together with the metacarpal section, middle section and/or the forearm section, when placed on, surround the hand, wrist or the forearm, wherein the bands at least partially run over the back of the hand, wrist and around the forearm, respectively. For example, the orthosis can have a first, second and third closure device (e.g. band) which run at least partially over the back of the hand, wrist and around the forearm, respectively. The first, second and third closure device (e.g. band) can be securable in attachment points in the metacarpal section, the metacarpal section and the middle section, and the forearm section, respectively.

The closure device has one or more first fastening sections which are arranged and configured in such a manner that, when the orthosis is placed on, said fastening sections can be arranged and secured on the metacarpal section and/or the forearm section in such a manner that said fastening sections in each case run over the back of the hand and forearm, respectively, and together with the metacarpal section and the forearm section, respectively, of the stiff body, forms at least a part of a section of the orthosis, which section annularly surrounds the hand and forearm, respectively. The orthosis can thereby be simply and securely held or secured on the hand and/or forearm by the first fastening section or the first fastening sections—either by themselves or together with further sections of the closure device. The closure device can also have one or more first fastening sections which are arranged and configured in such a manner that, when the orthosis is placed on, said fastening sections can be arranged and secured on the metacarpal section, the middle section and/or the forearm section in such a manner that said fastening sections in each case run over the back of the hand, wrist and/or forearm, respectively, and together with the metacarpal section, the middle section and the forearm section, respectively, of the stiff body, forms at least a part of a section of the orthosis, which section annularly surrounds the hand, wrist and/or forearm, respectively.

This closure device or at least the first fastening sections or at least one of the first fastening sections can either be provided as separate components which can be completely detached from the metacarpal section and the forearm section or the rest of the orthosis and can be connected again thereto for fastening purposes, or as components which are fastened permanently to the aforementioned sections. In the latter case, it can be provided in particular that the relevant first fastening sections are in each case permanently fastened at one point and, after arrangement such that they run over the back of the hand or forearm, can be fastened releasably for securing at another point.

First fastening sections of this type can be formed in an advantageous manner, for example, by a respective flexible and/or elastic band. For the releasable connection to the metacarpal section or forearm section, the bands can in each case have touch and close elements which can interact with corresponding, suitably arranged, different touch and close elements on the bands themselves or on the metacarpal or forearm section or on another part of the orthosis. In this connection, one or more openings, through which one or more of the bands can be guided in each case, can be provided at the first end or on a section connected to the latter. After passing through, each band can be fastened, for example, to itself, for example with the aid of the above-mentioned touch and close elements, thus, in each case producing a loop section which runs through one of the openings.

The first fastening section of the closure devices connected to the metacarpal section can, e.g. be connected to the thumb holding section of the metacarpal section. Alternatively, they can be connected to the ulnar section. One closure device preferably runs over the back of the hand connecting an area of the thumb holding section that is distal of the base of the thumb with the ulnar section. An alternative or additional closure device preferably runs over the back of the hand connecting an area of the thumb holding section that is proximal of the base of the thumb with the ulnar section. An alternative or addition closure device preferably runs over the back of the hand and wrist, thereby connecting an area of the ulnar section with the middle section. An alternative or additional closure device preferably runs over the forearm on a side that is opposite to a side of the forearm on which the stiff body is located, connecting one end of the forearm section with another end of the forearm section. Thereby, the latter closure device together with the forearm section of the stiff body encircles the forearm.

The attachment sites for attaching a first closure device, such as a band, to the stiff body can be located in an area of the thumb holding section that is distal of the base of the thumb and in the ulnar section. The attachment sites for attaching a second closure device, such as a band, to the stiff body can be located in an area of the thumb holding section that is proximal of the base of the thumb and in the ulnar section. Alternatively, the attachment sites for attaching a second closure device, such as a band, to the stiff body can be located in an area of the thumb holding section that is proximal of the base of the thumb and in the middle region. The attachment sites for attaching a third closure device, such as a band, to the stiff body can be located at two opposite ends of the forearm section. The orthosis of the invention can advantageously be used in the treatment or prevention of a human wrist injury or painful condition of the human wrist. The injury or condition may be an acute or chronic injury or condition. The treatment may comprise wearing the orthosis for one, two, three or more weeks. Further the treatment may comprise examination of and/or surgery on the affected wrist at a time when the orthosis is worn on the hand, wrist and forearm of said wrist.

In a second aspect, the invention relates to a method of the production of an orthosis according to the invention, i.e. an orthosis as described herein. Any of the aforementioned processes and materials can be used in the manufacture of the orthosis, in particular a method selected from the group consisting of 2-component (plastic) injection moulding, multi-component plastic injection moulding, metal core overmoulding or plastic overmoulding in general and metal mesh overmoulding. In a preferred embodiment, the method comprises metal core overmoulding.

In a third aspect, the invention relates to a method for the treatment or prevention of a human wrist injury or painful condition of the human wrist comprising donning an orthosis of the invention. The injury may be an acute or chronic injury. The treatment may comprise wearing the orthosis for one, two, three or more weeks. Further the treatment may comprise examination of and/or surgery on the affected wrist at a time when the orthosis is worn on the hand, wrist and forearm of said wrist. Advantageously, the orthosis does not cover the dorsal and ventral sides of the wrist in their entirety so that no additional stress or pressure is exerted on a potential wound or surgical site by the orthosis.

BRIEF DESCRIPTION OF FIGURES

Exemplary embodiments of the invention are shown schematically in the drawings.

FIG. 1 schematically shows a dorsal view of an orthosis according to the invention;

FIG. 2 schematically shows a ventral/palmar view of the orthosis of FIG. 1;

FIG. 3 schematically shows a perspective view of the orthosis of FIG. 1;

These and other aspects of the invention will be apparent from and elucidated with reference to the embodiments described hereinafter.

DETAILED DESCRIPTION

Additional advantages, characteristics, and features of the present invention will become clear from the following detailed description of exemplary embodiments with reference to the attached drawings. However, the invention is not restricted to these exemplary embodiments.

FIGS. 1 to 4 and FIGS. 6 to 11 schematically show two different embodiments of an orthosis 10 of the invention which comprises a stiff body 12. In fact, as shown in these figures, the orthosis 10 consists of the stiff body 12. The orthosis 10 does not comprise any closure devices 34, 36, 38 but these can be added at the respective attachment sites 40, 42, 44, 46, 48, 50 for closure devices as illustrated in FIGS. 12 to 14 and 15 to 19, respectively.

Figures 6, 7, 8:
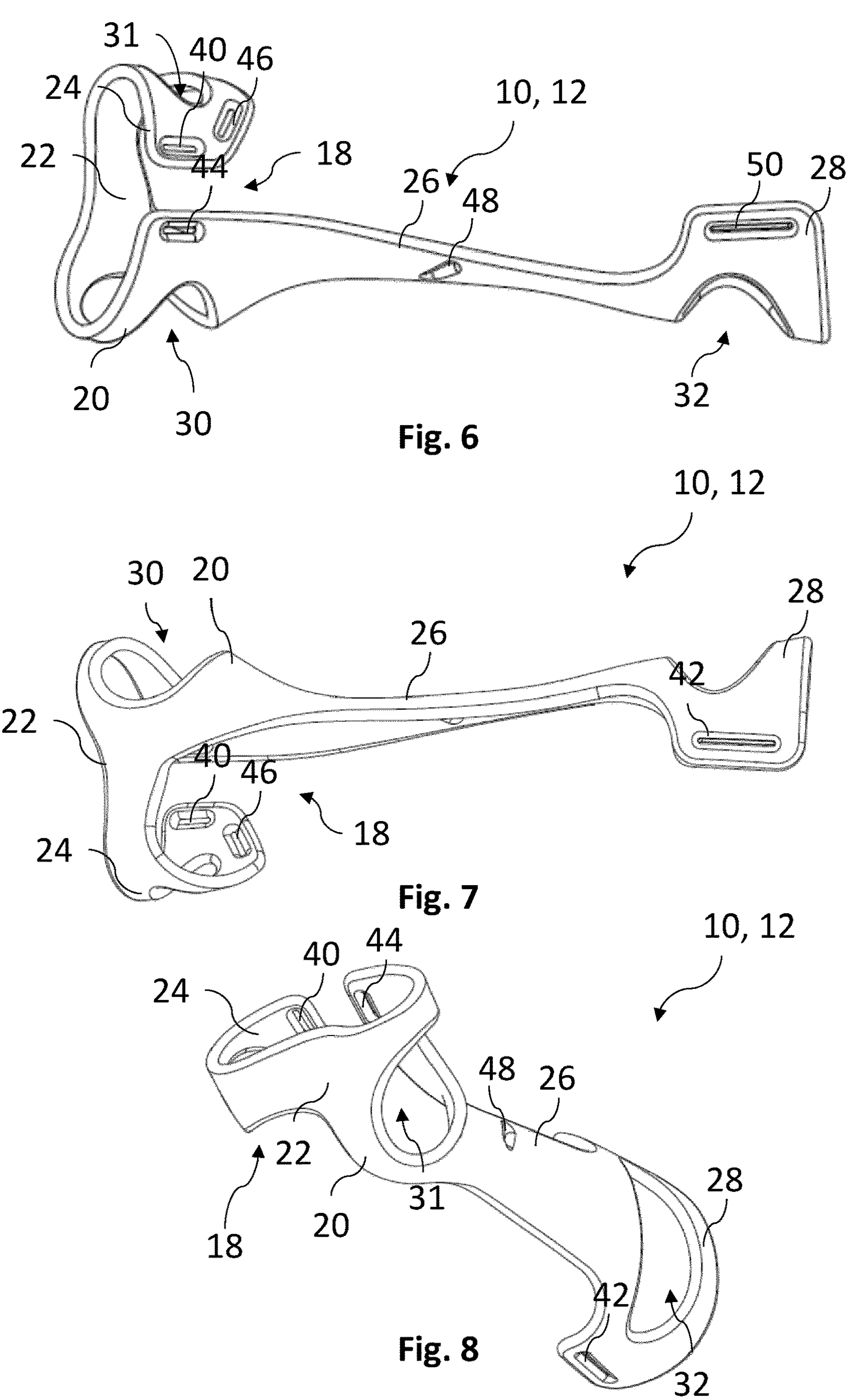
FIG. 6 schematically shows a dorsal view of another embodiment of an orthosis according to the invention.
FIG. 7 schematically shows a ventral/palmar view of the orthosis of FIG. 6.
FIG. 8 schematically shows a perspective view of the orthosis of FIG. 6.

FIG. 1 and FIG. 6 schematically show a dorsal view, FIG. 2 and FIG. 7 a ventral/palmar view, and FIGS. 3 and 4 and FIGS. 8, 9 and 10 different perspective views of the orthosis 10. FIG. 11 shows a view of the ulnar side and inner side of the orthosis 10. The orthosis 10 comprises a metacarpal section 18 which is suitable to be worn on the hand of a patient, in particular in the metacarpal region of the hand, specifically the palm and metacarpal side (ulnar and radial) regions of the hand. The metacarpal section 18 consists of a thumb holding section 20, a palmar section 22 and an ulnar section 24.

The thumb holding section 20 is ring-shaped and has an opening 30 in the middle of this ring shape through which the thumb of the wearer can pass. It can be seen that the thumb holding section 20 in the embodiment shown in FIG. 6 extends more to the dorsal side of the hand than the thumb holding section 20 in the embodiment shown in FIG. 1. The distance between the thumb holding section 20 and the ulnar section 24 in the embodiment shown in FIG. 6 is shorter when measured on the dorsal side of the orthosis 10 than in the embodiment shown in FIG. 1. The distance between the thumb holding section 20 and the ulnar section 24 on the dorsal side of the orthosis 10 is ⅓ or less of the width of the orthosis in the metacarpal section 18 as measured perpendicular to the longitudinal axis of the orthosis 10.

Figures 9, 10, 11:
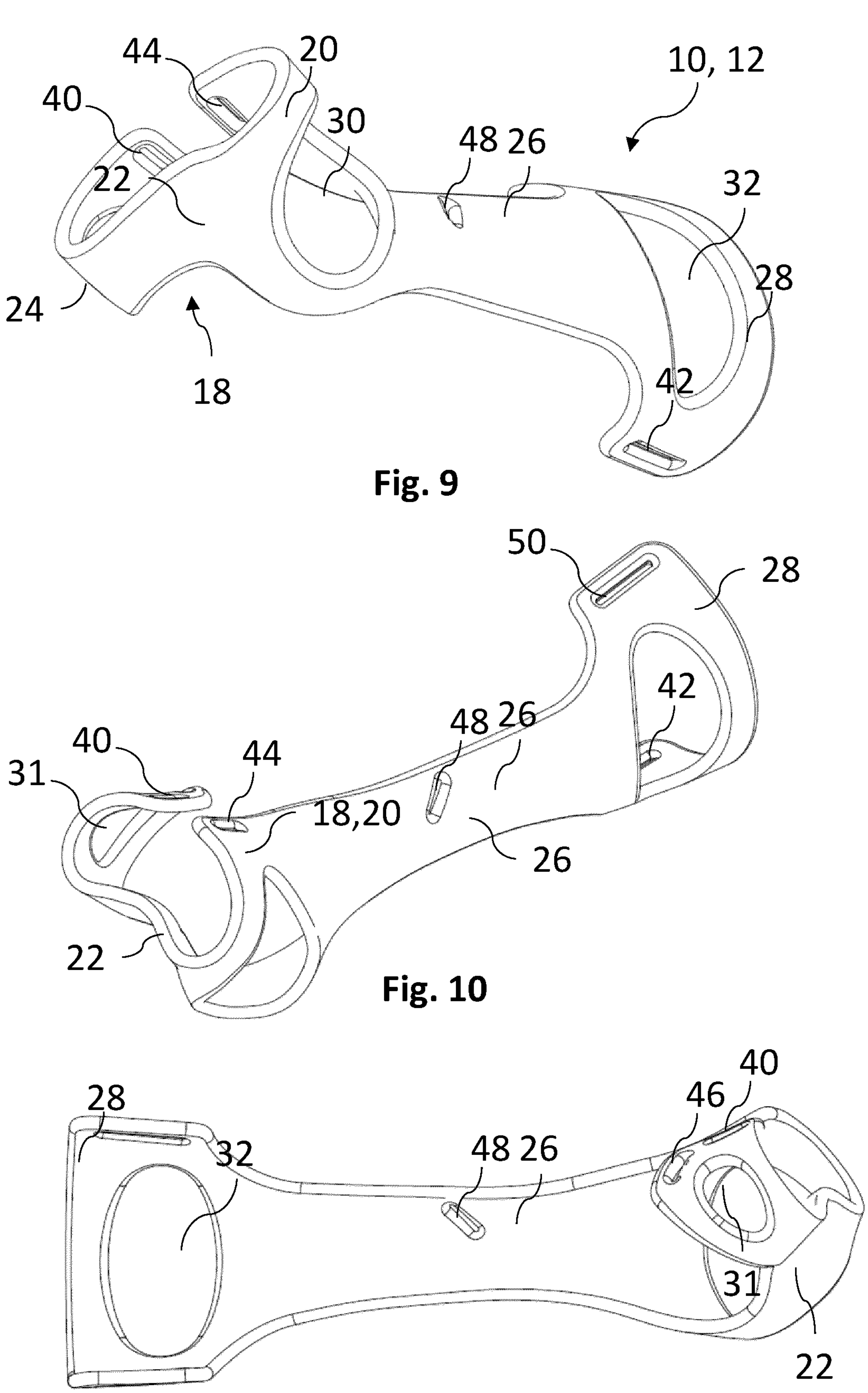
FIG. 9 schematically shows a second perspective view of the orthosis of FIG. 6.
FIG. 10 schematically shows a third perspective view of the orthosis of FIG. 6.
FIG. 11 schematically shows a view of a part of the inner side and the ulnar side of the orthosis of FIG. 6.

The palmar section 22 is designed to lie on the surface of the hand in the palm region. It has a long shape that is narrow enough not to interfere with the individual finger movements. Moreover, as can be seen in FIG. 10, it can have a concave shape, curving inwards towards the direction of the inner side of the orthosis, i.e. towards the palm when the orthosis is worn correctly.

Adjacent to the palmar section 22, the metacarpal section 18 comprises an ulnar section 24 which is designed to wrap around the area of the fifth bone of the metacarpal region from the ventral to the dorsal side of the hand. Ulnar section 24 comprises an opening 31 which makes the orthosis 10 lighter and the skin surface easier to access.

The orthosis 10 further comprises an elongated middle section 26 which has, in these embodiments, approximately the same length as the metacarpal section 18 and the forearm section 28. The middle section 26 is narrower than the other two sections of the orthosis 10, in circumferential direction, and is designed to extend along the radial side of the wrist and forearm. The middle section 26 covers mainly the radial side but is slightly bent to extend slightly also onto the ventral and dorsal sides of the wrist and arm. It can be seen that not more than 25% of the areas of the ventral and dorsal sides are covered by the ulnar section 24.

Proximally adjacent to the middle section 26, the orthosis 10 comprises a forearm section 28 which is adapted to extend around the forearm to a greater extent than the middle section 26. It nevertheless also covers and supports the forearm from the radial side. The forearm section 28 comprises an opening 32 which makes the orthosis 10 lighter and the skin surface easier to access.

The orthosis 10 comprises a number of six attachment sites 40, 42, 44, 46, 48, 50 which have the conformation of substantially rectangular holes in the stiff body 12, specifically its exostructure. Through these attachment sites 40, 42, 44, 46, 48, 50 closure devices can be inserted (not shown) and used for attachment of the orthosis 10 to the hand, wrist and forearm of a wearer. See FIGS. 12 to 14 and FIGS. 15 to 19 for exemplary embodiments which comprise such closure devices.

Figure 4:
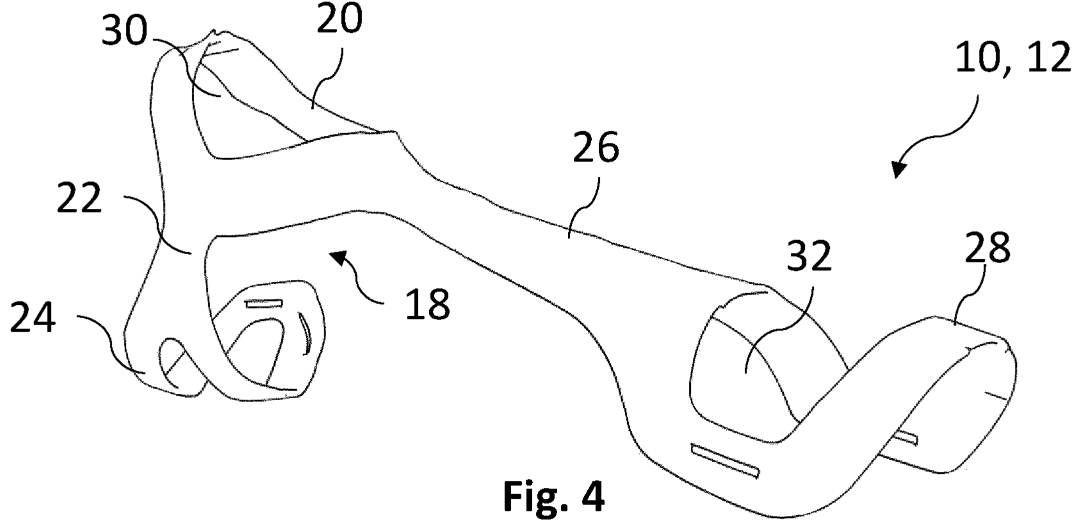
FIG. 4 schematically shows a second perspective view of the orthosis of FIG. 1.
Figure 5:
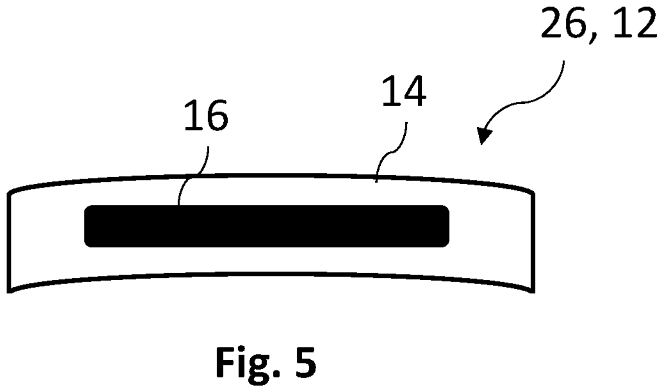
FIG. 5 schematically shows a cross-section of the middle section of the orthosis of FIG. 1.

FIG. 5 schematically shows a cross-section of the middle section 26 of the orthosis of FIGS. 1 to 4. It can be seen that the stiff body 12 in the middle section 26 consists of an exostructure 14 and a core 16 which is enclosed by the exostructure 14. The core 16 consists of an aluminium alloy metal and is ductile. The exostructure 14 is overmoulded onto the core 16 and consists of thermoplastic polyurethane (TPU). The embodiments shown in FIGS. 6 to 19 have the same construction of exostructure 14 and core 16 (not shown).

Figures 12, 13, 14:
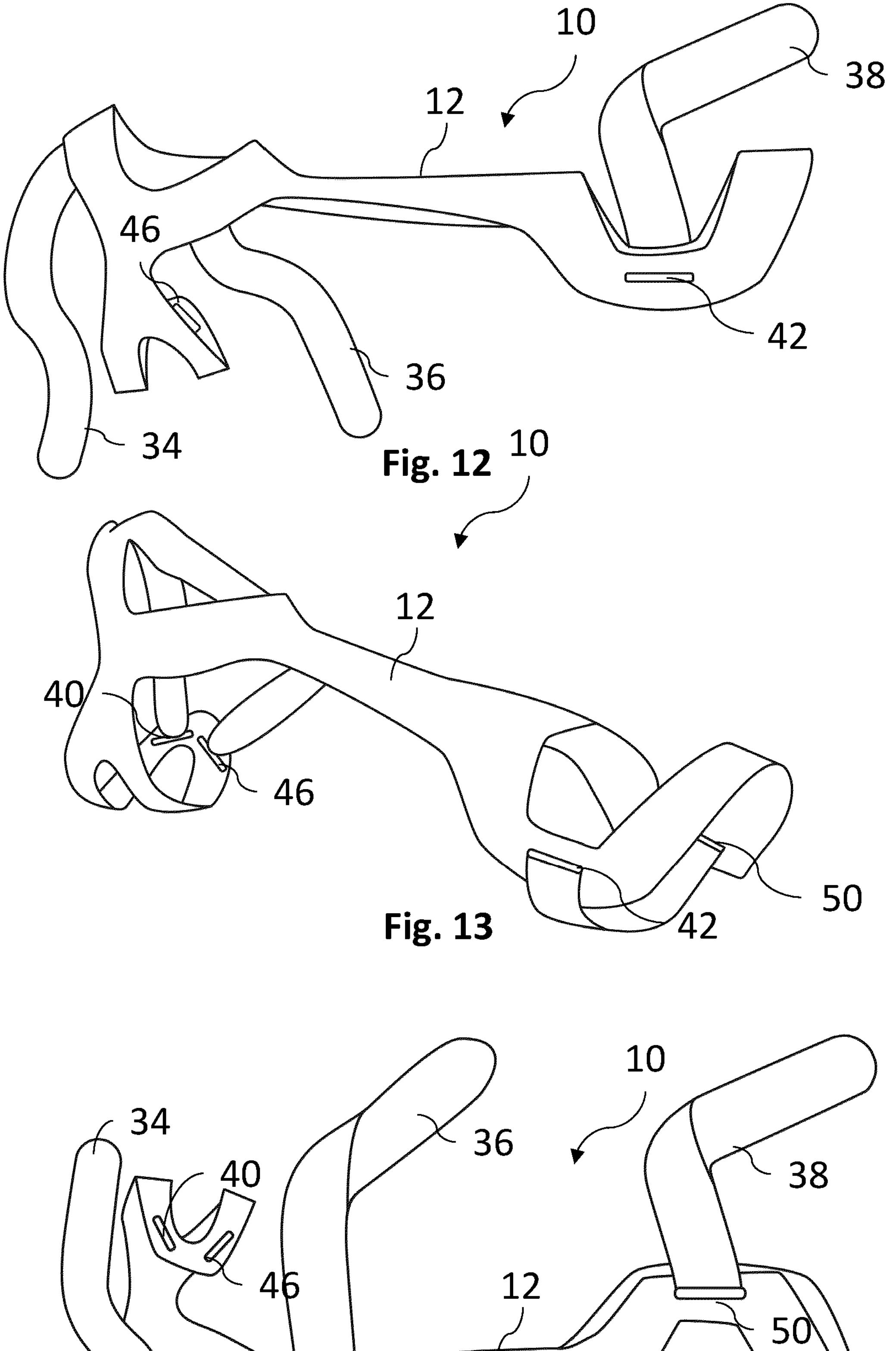
FIG. 12 shows a ventral/palmar view of another embodiment of the orthosis of the invention which comprises closure devices.
FIG. 13 shows a perspective view of the orthosis of FIG. 12.
FIG. 14 shows a dorsal view of the orthosis of FIG. 12.
Figures 15, 16, 17:
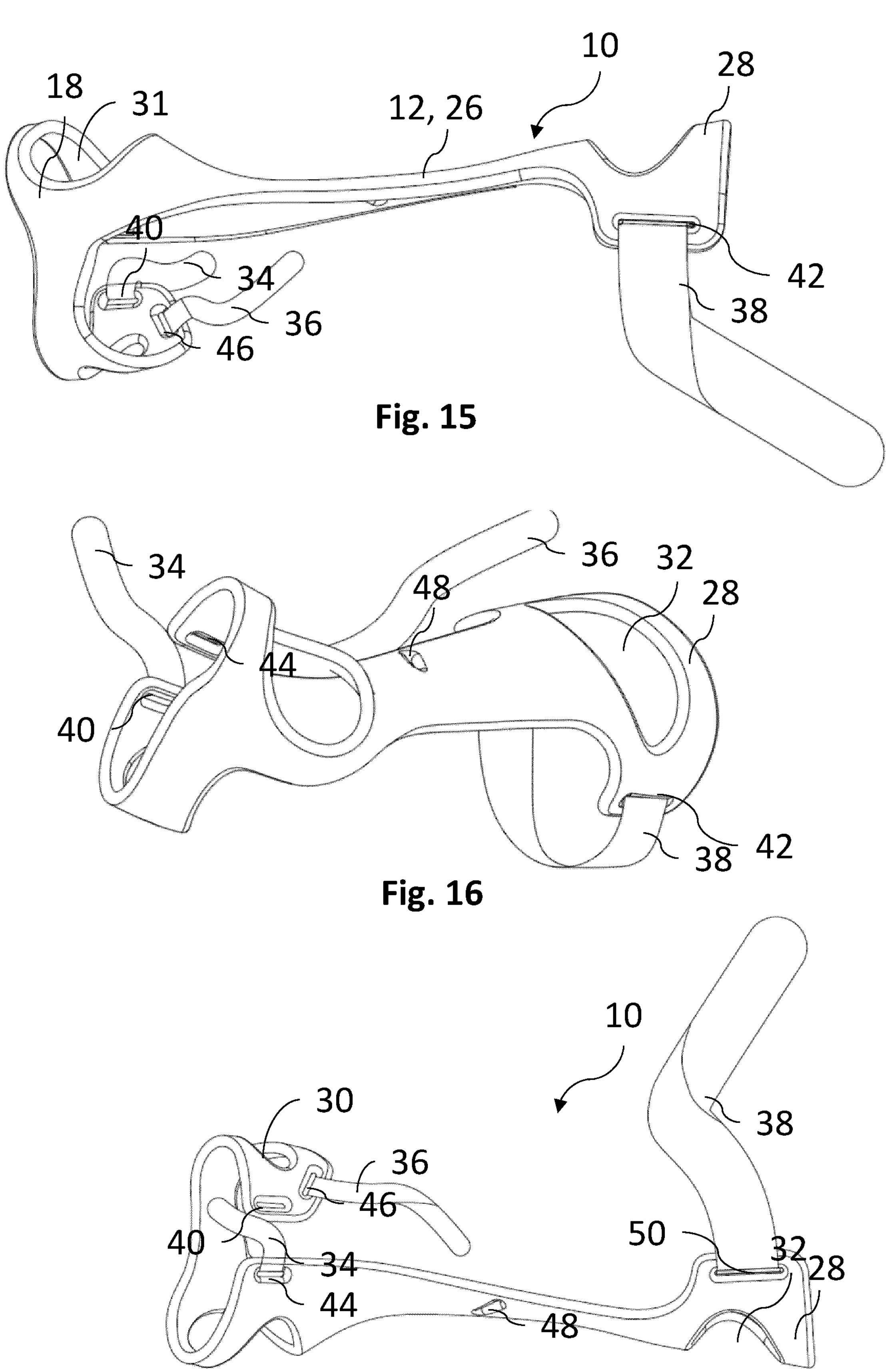
FIG. 15 shows a ventral/palmar view of another embodiment of the orthosis of the invention which comprises closure devices.
FIG. 16 shows a perspective view of the orthosis of FIG. 15.
FIG. 17 shows a dorsal view of the orthosis of FIG. 15.
Figure 18:
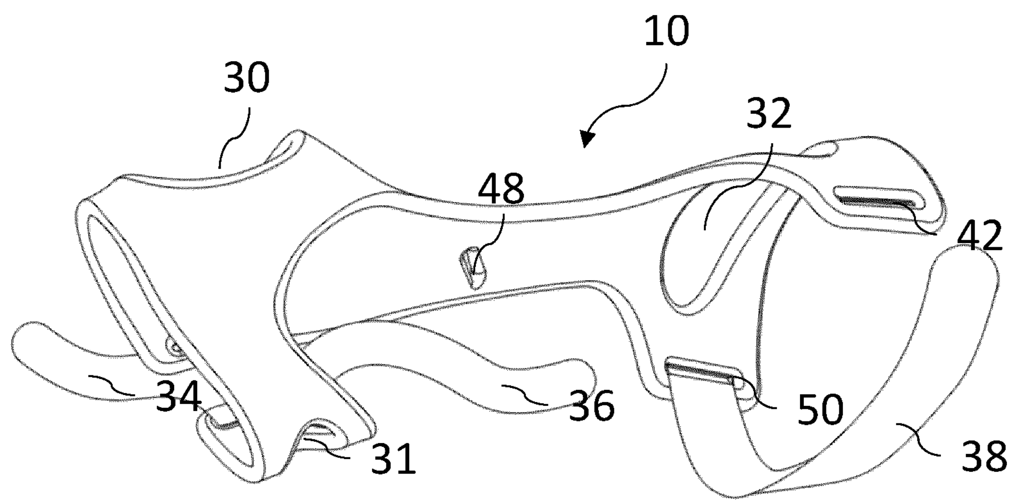
FIG. 18 shows a second perspective view of the orthosis of FIG. 15.
Figure 19:
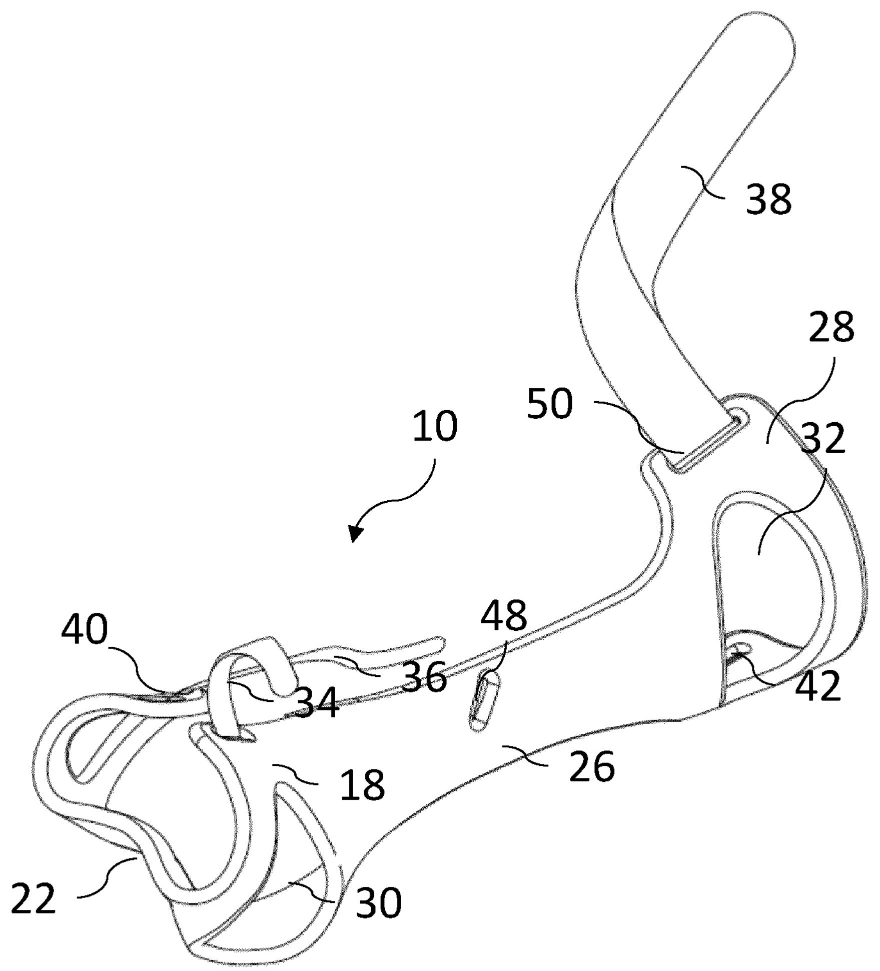
FIG. 19 shows a third perspective view of the orthosis of FIG. 15.

FIGS. 12 to 14 and FIGS. 15 to 19 schematically show other embodiments of the orthosis 10 of the invention which comprise a stiff body 12 and closure devices 34, 36 and 38. FIG. 12 and FIG. 15 show ventral/palmar views, FIG. 13 and FIGS. 16, 18 and 19 perspective views and FIG. 14 and FIG. 17 a dorsal views of the orthosis 10. The stiff body 12 of the orthosis 10 is substantially identical to the stiff body 12 shown in FIGS. 1 to 4 and FIGS. 6 to 11, respectively. The respective description of FIGS. 1 to 4 and FIGS. 6 to 11, thus, also applies to FIGS. 12 to 14 and FIGS. 15 to 19, respectively.

Furthermore, the orthoses 10 of FIGS. 12 to 14 and FIGS. 15 to 19 comprise the closure devices 34, 36 and 38 which have an elongated strap shape. One end region of each closure devices 34, 36 and 38 is fastened to an attachment site 44, 48, 50 each. The closure devices 34, 36 and 38 are polyamide straps. The end regions are welded to form a loop which fastens the closure devices 34, 36 and 38 in the first attachment sites 44, 48, 50. The straps can be passed through the opposite, second attachment sites 40, 46, 42, respectively, and then returned into the direction of the first attachment sites 44, 48, 50. The closure devices 34, 36 and 38 are closed with a Velcro, hook and loop fastening system. The first closure device 34 can be fastened between attachment sites 40, 44 in the ulnar section 24 and the thumb holding section 20. It can be seen that the second closure device 36 can be fastened between attachment sites 46, 48 in the ulnar section 24 and the thumb holding section 20 (FIGS. 12 to 14) or between attachment sites 46, 48 in the ulnar section 24 and the middle section 26 (FIGS. 15 to 19). The third closure device 38 can be fastened between attachment sites 42, 50 on opposite ends of the forearm section 28.

Figure 20:
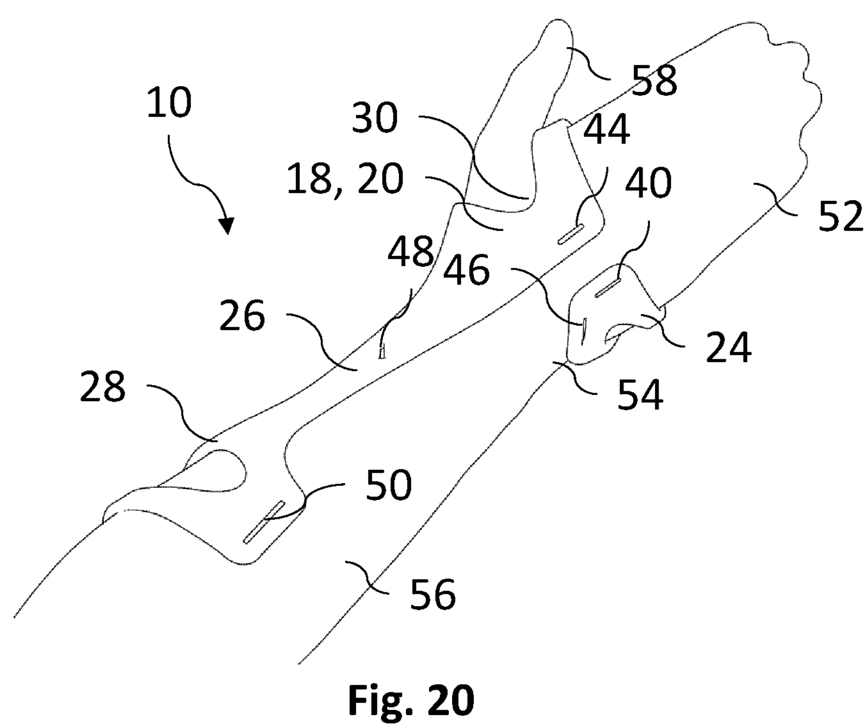
FIG. 20 shows a dorsal view of the orthosis of FIG. 15 when applied to a human forearm, wrist and hand.
Figure 21:
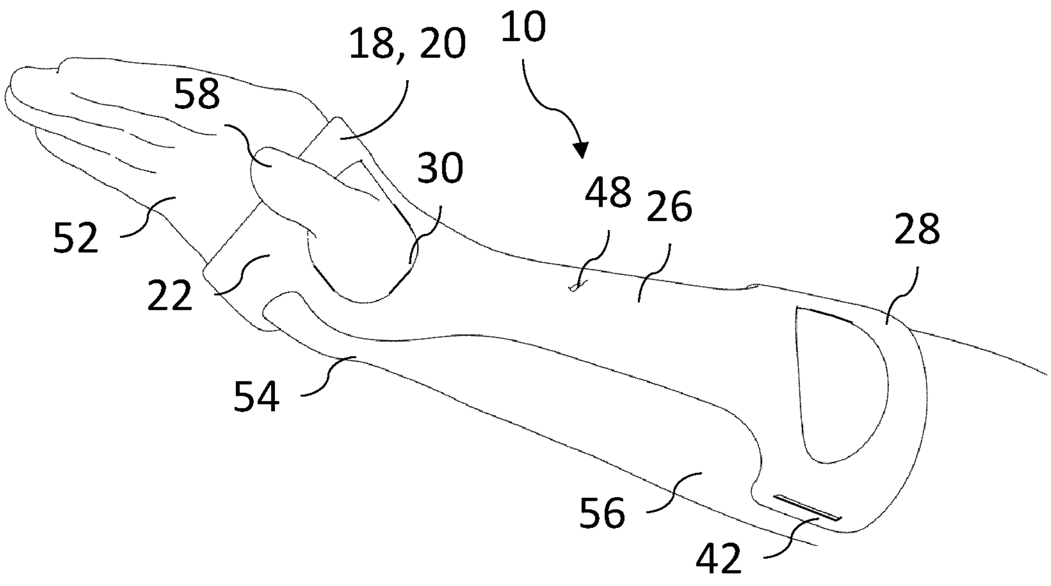
FIG. 21 shows a perspective view of the orthosis of FIG. 15 when applied to a human forearm, wrist and hand.

FIG. 20 and FIG. 21 show a dorsal and perspective view, respectively, of the orthosis 10 of FIG. 15 when applied to a human forearm 56, wrist 54 and hand 52. It can be seen that the thumb 58 fits through the opening 30. The thumb 58 is still movable, i.e. the movement of the thumb 58 is not prevented by the orthosis 10. At the same time, the orthosis 10 is able to stabilize the wrist 54 in an angled position. The wrist 54 is substantially immobilized, i.e. movements of the wrist in any direction are prevented. While FIGS. 20 and 21 only show an orthosis 10 consisting of a stiff body 12, closure devices 34, 36, 38 can, of course be attached to the stiff body 12 at the attachment sites 40, 42, 44, 46, 48, 50 to secure the orthosis 10.

Although the present invention has been described in detail with reference to the exemplary embodiments, it is obvious to those skilled in the art that the invention is not restricted to these exemplary embodiments, but rather that modifications can be made in such a way that individual features are omitted or other combinations of the individual features presented are realized, provided that the scope of protection of the appended claims is not exceeded. The present disclosure includes any and all combinations of the individual features presented.

REFERENCE SIGNS LIST

10 orthosis
12 stiff body
14 exostructure
16 core
18 metacarpal section
20 thumb holding section
22 palmar section
24 ulnar section
26 middle section
28 forearm section
30 opening
31 opening
32 opening
34 closure device
36 closure device
38 closure device
40 attachment site
42 attachment site
44 attachment site
46 attachment site
48 attachment site
50 attachment site
52 hand
54 wrist
56 forearm
58 thumb

The invention claimed is:

1. An orthosis adapted to be worn on a human forearm and hand for immobilizing the wrist joint, comprising a stiff body having an exostructure enclosing an elongated core, wherein the exostructure comprises or consists of a thermoplastic material, and wherein the stiff body comprises:

(i) a metacarpal section a. having a ring-shaped or ring-segment-shaped thumb holding section adapted to receive the thumb of the human hand, b. having a palmar section adapted to be brought into engagement with the palm of the human hand, and c. having an ulnar section adapted to wrap around the human hand from the volar to the dorsal side, (ii) an elongated middle section adapted to be brought into engagement with the human forearm, and, optionally, wrist, on their medial or lateral side, the elongated middle section being connected to only the thumb holding section of the metacarpal section; and (iii) a forearm section adapted to wrap around the human forearm from its ventral to its dorsal side;

wherein an axial length at the palmar section, measured parallel to the longitudinal axis of the orthosis, is less than an axial length of both the thumb holding section and the ulnar section.

2. The orthosis according to claim 1, wherein the core is reversibly plastically deformable.

3. The orthosis according to claim 1, wherein the stiff body consists of the exostructure and core.

4. The orthosis according to claim 1, wherein the middle section has a length that is 100% or more of the length of the metacarpal section when measured parallel to the longitudinal axis of the orthosis.

5. The orthosis according to claim 1, wherein the middle section has a length that is 125% or more of the length of the forearm section when measured parallel to the longitudinal axis of the orthosis.

6. The orthosis according to claim 1, wherein the exostructure is continuous from the ulnar section, the palmar section, the thumb holding section, the elongated middle section to the forearm section.

7. The orthosis according to claim 1, wherein the middle section is adapted to cover the wrist and/or forearm of a human on 50% or less of their respective circumferences.

8. The orthosis according to claim 1, wherein the forearm section is adapted to cover the forearm of a human on 25% to 90% of its circumference.

9. The orthosis according to claim 1, wherein the metacarpal section and/or the forearm section comprise an opening.

10. The orthosis according to claim 1, wherein the ulnar section comprises an opening on the ulnar side of the orthosis.

11. The orthosis according to claim 1, wherein the core consists of or comprises one or more metals or metal alloys and/or thermoplastic materials.

12. The orthosis according to claim 11, wherein the metal or metal alloys are selected from the group consisting of aluminium, iron, and alloys thereof.

13. The orthosis according to claim 1, wherein the exostructure comprises or consists of thermoplastic polyurethane, thermoplastic elastomer, thermoplastic rubber, silicone, and mixtures thereof.

14. The orthosis according to claim 1, wherein the stiff body is manufactured by a method selected from the group consisting of 2-component injection molding, multi-component plastic injection molding, metal core overmolding or plastic overmolding in general and metal mesh overmolding.

15. The orthosis according to claim 1, wherein the core extends from the metacarpal section, through the middle section and into the forearm section.

16. The orthosis according to claim 1, comprising one or more closure devices for fastening the orthosis on the human hand.

17. The orthosis according to claim 16, wherein one or two of the closure devices are attached to the metacarpal section and/or wherein one of the closure devices is attached to the forearm section.

18. The orthosis according to claim 1, for use in the treatment or prevention of a human wrist injury or painful condition of the human wrist.

19. Method of the production of an orthosis according to claim 1, using a method selected from the group consisting of 2-component injection molding, multi-component plastic injection molding, metal core overmolding or plastic overmolding in general and metal mesh overmolding.

20. An orthosis adapted to be worn on a human forearm and hand for immobilizing the wrist joint, comprising a stiff body having an exostructure enclosing an elongated core, wherein the exostructure comprises or consists of a thermoplastic material, and wherein the stiff body comprises:

(i) a metacarpal section a. having a ring-shaped or ring-segment-shaped thumb holding section adapted to receive the thumb of the human hand, b. having a palmar section adapted to be brought into engagement with the palm of the human hand, and c. having an ulnar section adapted to wrap around the human hand from the volar to the dorsal side, (ii) an elongated middle section adapted to be brought into engagement with the human forearm, and, optionally, wrist, on their medial or lateral side, the elongated middle section being connected to only the thumb holding section of the metacarpal section; and (iii) a forearm section adapted to wrap around the human forearm from its ventral to its dorsal side;

wherein the elongated middle section is engageable with only a radial side of the forearm, and the forearm section extends from the radial side of the forearm toward an ulnar side of the forearm in both a first direction and a second direction.

* * * * *